(12) United States Patent
Hensley

(10) Patent No.: US 8,026,290 B2
(45) Date of Patent: Sep. 27, 2011

(54) METHODS AND APPARATUS FOR CONTINUOUS REMOVAL OF CARBON DIOXIDE FROM A MIXTURE OF REACTING GASES

(75) Inventor: Jesse E. Hensley, Arvada, CO (US)

(73) Assignee: Range Fuels, Inc., Denver, CO (US)

( * ) Notice: Subject to any disclaimer, the term of this patent is extended or adjusted under 35 U.S.C. 154(b) by 186 days.

(21) Appl. No.: 12/252,545

(22) Filed: Oct. 16, 2008

(65) Prior Publication Data
US 2009/0149558 A1    Jun. 11, 2009

Related U.S. Application Data

(60) Provisional application No. 61/012,895, filed on Dec. 11, 2007, provisional application No. 61/012,898, filed on Dec. 11, 2007.

(51) Int. Cl.
*C07C 27/00* (2006.01)
*C01B 17/16* (2006.01)
(52) U.S. Cl. ........................................ 518/700; 423/220
(58) Field of Classification Search .................. 518/700; 423/220
See application file for complete search history.

(56) References Cited

U.S. PATENT DOCUMENTS

| | | | |
|---|---|---|---|
| 5,449,696 A | 9/1995 | Dandekar et al. | |
| 6,303,092 B1 | 10/2001 | Anand et al. | |
| 6,692,545 B2 | 2/2004 | Gittleman et al. | |
| 2004/0220443 A1 | 11/2004 | Degraaf et al. | |
| 2007/0010588 A1 | 1/2007 | Pearson | |
| 2007/0259972 A1 | 11/2007 | Lattner et al. | |
| 2008/0156190 A1* | 7/2008 | Lutz et al. | 95/148 |
| 2010/0068109 A1* | 3/2010 | Comrie | 423/220 |
| 2010/0069515 A1* | 3/2010 | Tirtowidjojo et al. | 518/705 |

OTHER PUBLICATIONS

Pio Forzatti et al., "Higher Alcohol Synthesis", Catalysis Reviewsl, 33:1, 109-168 (Feb. 1, 1991).

* cited by examiner

*Primary Examiner* — Jafar Parsa
(74) *Attorney, Agent, or Firm* — O'Connor & Company; Ryan P. O'Connor

(57) ABSTRACT

The disclosed invention provides methods and apparatus for producing one or more $C_1$-$C_4$ alcohols (such as ethanol) from syngas, while simultaneously removing $CO_2$, thereby providing low $CO_2$ yields. The present invention provides reactors for producing one or more $C_1$-$C_4$ alcohols from syngas, the reactors containing a first composition capable of catalyzing the conversion of syngas to $C_1$-$C_4$ alcohols under reaction conditions and a second composition capable of (a) adsorbing $CO_2$ under the reaction conditions and then (b) releasing at least some of the $CO_2$ under different regeneration conditions.

26 Claims, 3 Drawing Sheets

METHODS AND APPARATUS FOR CONTINUOUS REMOVAL OF CARBON DIOXIDE FROM A MIXTURE OF REACTING GASES

FIELD OF THE INVENTION

The present invention generally relates to the field of processes for the chemical conversion of synthesis gas to alcohols, such as ethanol.

BACKGROUND OF THE INVENTION

Synthesis gas (hereinafter referred to as syngas) is a mixture of hydrogen ($H_2$) and carbon monoxide (CO). Syngas can be produced, in principle, from virtually any material containing carbon. Carbonaceous materials commonly include fossil resources such as natural gas, petroleum, coal, and lignite; and renewable resources such as lignocellulosic biomass and various carbon-rich waste materials. It is preferable to utilize a renewable resource to produce syngas because of the rising economic, environmental, and social costs associated with fossil resources.

There exist a variety of conversion technologies to turn these feedstocks into syngas. Conversion approaches can utilize a combination of one or more steps comprising gasification, pyrolysis, steam reforming, and/or partial oxidation of a carbon-containing feedstock.

Syngas is a platform intermediate in the chemical and biorefining industries and has a vast number of uses. Syngas can be converted into alkanes, olefins, oxygenates, and alcohols. These chemicals can be blended into, or used directly as, diesel fuel, gasoline, and other liquid fuels. Syngas can also be directly combusted to produce heat and power.

Since the 1920s it has been known that mixtures of methanol and other alcohols can be obtained by reacting syngas over certain catalysts (Forzatti et al., *Cat. Rev.-Sci. and Eng.* 33(1-2), 109-168, 1991). Fischer and Tropsch observed around the same time that hydrocarbon-synthesis catalysts produced linear alcohols as byproducts (Fischer and Tropsch, *Brennst.-Chem.* 7:97, 1926).

Currently, catalytic reactors used for selective formation of alcohols from syngas do not completely consume the reactants CO and $H_2$ in a single reactor pass. Further, these reactors can produce $CO_2$, which dilutes the reactant stream, slows the formation of alcohols, and participates in the reverse water-gas shift reaction, thereby producing water. It is desired that unreacted CO and $H_2$ be recycled to the reactor, substantially without $CO_2$, to prevent buildup of $CO_2$ and subsequent lowering of alcohol yields.

What are needed, therefore, are methods, and apparatus for carrying out the methods, for removal of $CO_2$ from a reaction mixture containing reactants (CO and $H_2$) and products (paraffins, $CO_2$, $H_2O$, alcohols, carbonyl compounds, and olefins), followed by recycle of non-condensable gases from reactor effluent. These methods and apparatus would effectively combine separation and chemical reactions.

SUMMARY OF THE INVENTION

This invention effectively enables the removal of carbon dioxide from a reaction mixture while the carbon dioxide is being formed inside a reactor.

Some embodiments of the present invention provide a method for producing one or more $C_1$-$C_4$ alcohols from syngas, the method comprising:

(i) converting a portion of the syngas into one or more $C_1$-$C_4$ alcohols using a first composition that can catalyze the conversion of syngas to $C_1$-$C_4$ alcohols under reaction conditions in a reactor;

(ii) capturing a portion of the carbon dioxide produced or present, using a second composition that is capable of adsorbing carbon dioxide under the reaction conditions; and (iii) releasing at least some of the carbon dioxide from the second composition under regeneration conditions, wherein the first composition and the second composition are both contained in the reactor, and wherein the reaction conditions are different from the regeneration conditions.

In some embodiments, the second composition is substantially chemically inert under the reactor conditions. In some embodiments, the second composition comprises a zeolite, such as a zeolite selected from the Faujasite structure class. Exemplary zeolites include Zeolite 4A and Zeolite 13X. In other embodiments, the second composition does not include a zeolite. For example, the second composition can comprise calcium oxide and other adsorbent materials.

During step (ii), at least some water produced or present can be adsorbed onto the second composition, in some embodiments. Additionally, during step (ii), the second composition can adsorb chemicals such as, but not limited to: methane, ethane, ethylene, propane, sulfur dioxide, and hydrogen sulfide.

In some embodiments, the second composition is capable of being regenerated by decreasing pressure and/or increasing temperature. In some embodiments, the first and second compositions are combined prior to loading into the reactor. The first and second compositions can be layered, at least in part, in the reactor. Or, the second composition can reside substantially adjacent to an outlet of the reactor (i.e., near the reactor exit). The second composition can be present in the form of pellets or other geometries to help reduce pressure drop.

In certain embodiments of the invention, step (iii) is conducted in-situ in the reactor. In other embodiments, step (iii) is conducted ex-situ (outside the syngas-to-alcohol reactor). Step (iii) can utilize a reduction in pressure, an increase in temperature, or both of these. Step (iii) can include pressure-swing adsorption. Optionally, at least one condensable species can be removed from the reactor prior to conducting step (iii).

In some embodiments, step (iii) further comprises placing the reactor under a substantially inert gas. An inert gas can be introduced prior to step (iii), during step (iii), or between a plurality of repetitions of step (iii).

These steps can be repeated after regeneration (removal of $CO_2$). Fresh or recycled syngas can be introduced in accordance with step (i).

In certain preferred embodiments, which are by no means limiting, step (ii) is capable of capturing at least 80% of the carbon dioxide present in the stream from step (i). In preferred embodiments, step (iii) is capable of releasing at least 90% of the carbon dioxide captured in step (ii). Preferably, step (ii) is capable of capturing at least 90% of the carbon dioxide present in the stream from step (i), and step (iii) is capable of releasing at least 95% of the carbon dioxide captured in step (ii).

In a specific embodiment, a method is provided for producing ethanol from syngas, the method comprising:

(i) converting a portion of the syngas into ethanol using a catalyst composition that can catalyze the conversion of syngas to ethanol under reaction conditions in a reactor;

(ii) capturing a portion of the carbon dioxide produced or present, using an adsorbent composition contained in the reactor, wherein the adsorbent composition is capable of adsorbing carbon dioxide under the reaction conditions and is substantially chemically inert under the reactor conditions; and (iii) releasing at least some of the carbon dioxide from the second composition under regeneration conditions comprising a lower pressure and/or a higher temperature than the reaction conditions.

Other embodiments of the invention provide an apparatus for producing one or more $C_1$-$C_4$ alcohols from syngas, the apparatus comprising a first composition that is capable of catalyzing the conversion of syngas to $C_1$-$C_4$ alcohols under reaction conditions, and a second composition that is capable of (a) adsorbing carbon dioxide under the reaction conditions and (b) releasing at least some of the carbon dioxide under regeneration conditions. In some embodiments, the second composition in the apparatus comprises zeolites; other embodiments do not employ zeolites.

DETAILED DESCRIPTION OF EMBODIMENTS OF THE INVENTION

Figure 1:
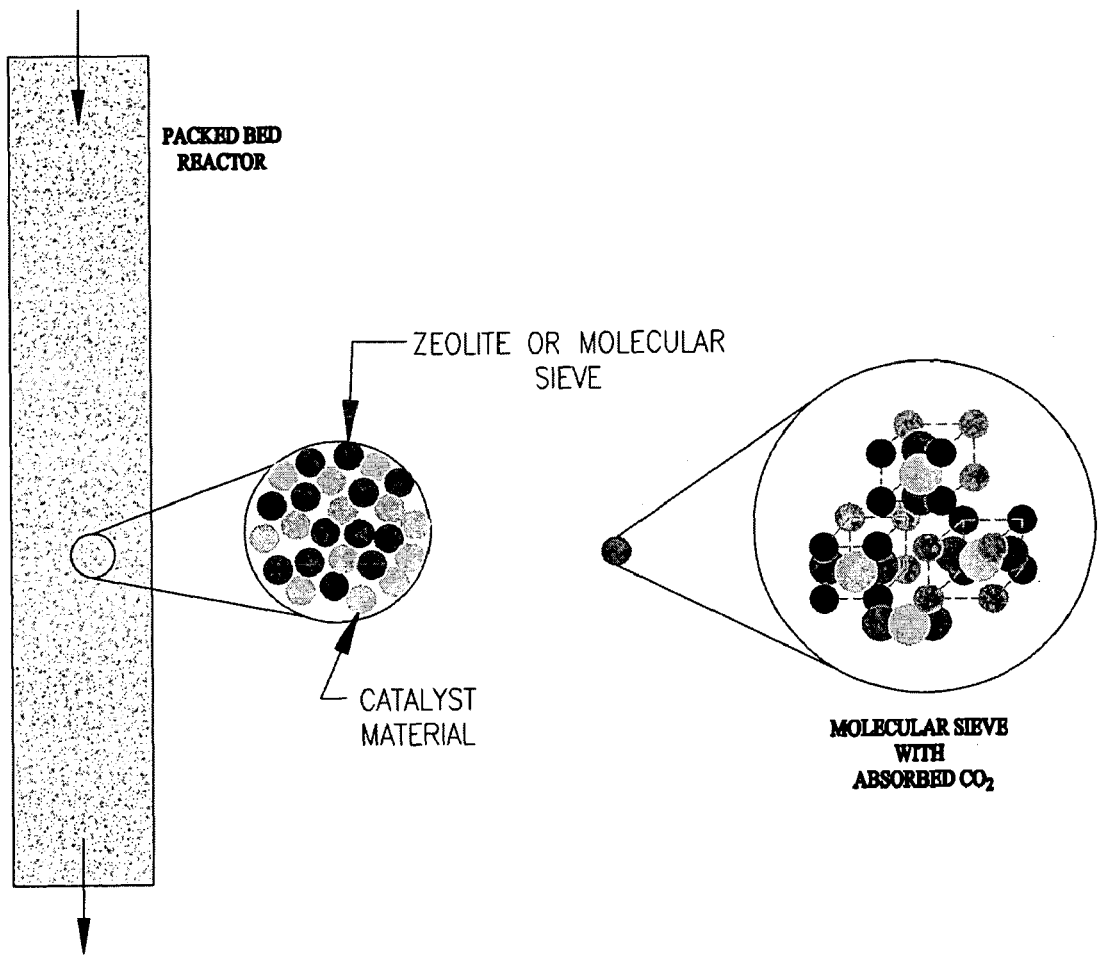
FIG. 1 is a schematic representation of zeolite/molecular sieve dispersed in a catalyst bed, with adsorbed $CO_2$ molecules, in some embodiments.

This description will enable one skilled in the art to make and use the invention, and it describes several embodiments, adaptations, variations, alternatives, and uses of the invention, including what is presently believed to be the best mode of carrying out the invention.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and claims are approximations that may vary depending at least upon the specific analytical technique. Any numerical value inherently contains certain errors necessarily resulting from the standard deviation found in its respective testing measurements.

As used herein, "$C_1$-$C_4$ alcohols" means one or more alcohols selected from methanol, ethanol, propanol, and butanol, including all known isomers of such compounds. While preferred embodiments are described in relation to high selectivities to ethanol, the invention can also be practiced in a manner that gives high selectivities to propanol and/or butanol, or certain combinations of selectivities to ethanol, propanol, and butanol, depending on the desired fuel attributes.

The present invention will now be described by reference to the following detailed description and accompanying drawings which characterize and illustrate some preferred embodiments for producing ethanol. This description by no means limits the scope and spirit of the present invention.

In one aspect of the present invention, an adsorbent material is provided, wherein the adsorbent material can remove carbon dioxide ($CO_2$) from a reaction mixture while it is being formed inside a reactor. The adsorbent material should have a high affinity for $CO_2$ and water and a low affinity for alcohols and CO. The material preferably has a microporous structure, such as that found in many types of zeolites, and is preferably stable under reactor conditions which can be selected as described below. In some embodiments, the adsorbent material is in the form of balls or pellets, for the purpose of minimizing reactor pressure drop.

In some embodiments, reactors can contain a catalytic material upon which chemical reactions take place. Heat is released due to the exothermic chemical reactions that preferably produce alcohols. This heat can damage the catalyst if the heat is localized or non-uniform, due to local temperature extremes (also known as "hot spots"). To prevent this damage, the catalyst can be dispersed in an inert material such as alumina powder, to prevent formation of hot spots within the reactor.

In another aspect of the present invention, the inert material described in the previous paragraph can be replaced by the adsorbent materials provided according to the invention. In this aspect, the materials can serve a dual role as an adsorbent for $CO_2$ and water, as well as a catalyst separator to delocalize the heat of reaction. The adsorbent materials can help maintain uniform temperatures within the reactor.

In some embodiments, the adsorbent materials are zeolites. Zeolites are, basically, hydrated aluminosilicate minerals with microporous structures. Generally, zeolites are the aluminosilicate members of the family of microporous solids known as "molecular sieves." Molecular sieves possess the ability to selectively sort molecules based primarily on a size-exclusion process, and sometimes based primarily on differences in the affinities of molecules to adsorb on the molecular-sieve surfaces.

In preferred embodiments, the adsorbent materials have at least some affinity to small polar molecules. Also, it is preferred that the adsorbent materials are substantially chemically inert under reactor conditions. FIG. 1 shows a schematic of exemplary adsorbent materials that can be used for the methods and apparatus herein.

Preferred materials for the present invention include zeolites of the Faujasite structure class, such as Zeolite 13X, and Zeolite 4A, which are commercially available from, for example, Zeolyst in Pennsylvania, U.S. One of ordinary skill in the art will recognize and appreciate that materials other than those recited can be employed, including both zeolites and non-zeolites (such as calcium oxide).

In preferred embodiments, the adsorbent material is capable of being regenerated. Such regeneration can be accomplished, for example, by decreased pressure and/or increased temperature, whereby adsorbed $CO_2$ can be released from the adsorbent material and can exit the reactor. The adsorbent material preferably can tolerate the elevated temperatures at which desorption is favored. In certain embodiments, one or more reactor tubes can be shut and pressure released from them, as a method of regenerating adsorbent.

In some embodiments, the adsorbent material is blended with catalyst material, followed by loading the combined material into a reactor. Alternatively, catalyst and adsorbent can be layered in a reactor tube, with certain spacing (such as even spacing) between adsorbent layers. Another option is to have the adsorbent reside primarily near the reactor exit.

When the adsorbent material has reached its absorptive capacity (as evidenced by significant quantities of $CO_2$ in the reactor effluent) or after some prescribed amount of time, the adsorbent material can be regenerated. In some embodiments, the reactor is first placed under an inert gas for protection of the catalyst. In some embodiments, the pressure within the reactor is decreased to release adsorbed $CO_2$; alternately, or in addition, the temperature within the reactor can be increased to release adsorbed $CO_2$. In other embodiments, the reactor is not placed under an inert gas for protection but the pressure within the reactor is reduced to release adsorbed $CO_2$. After $CO_2$ is released from the adsorbent material, reactants can be reintroduced at the preferred process temperature and pressure.

Figure 2:
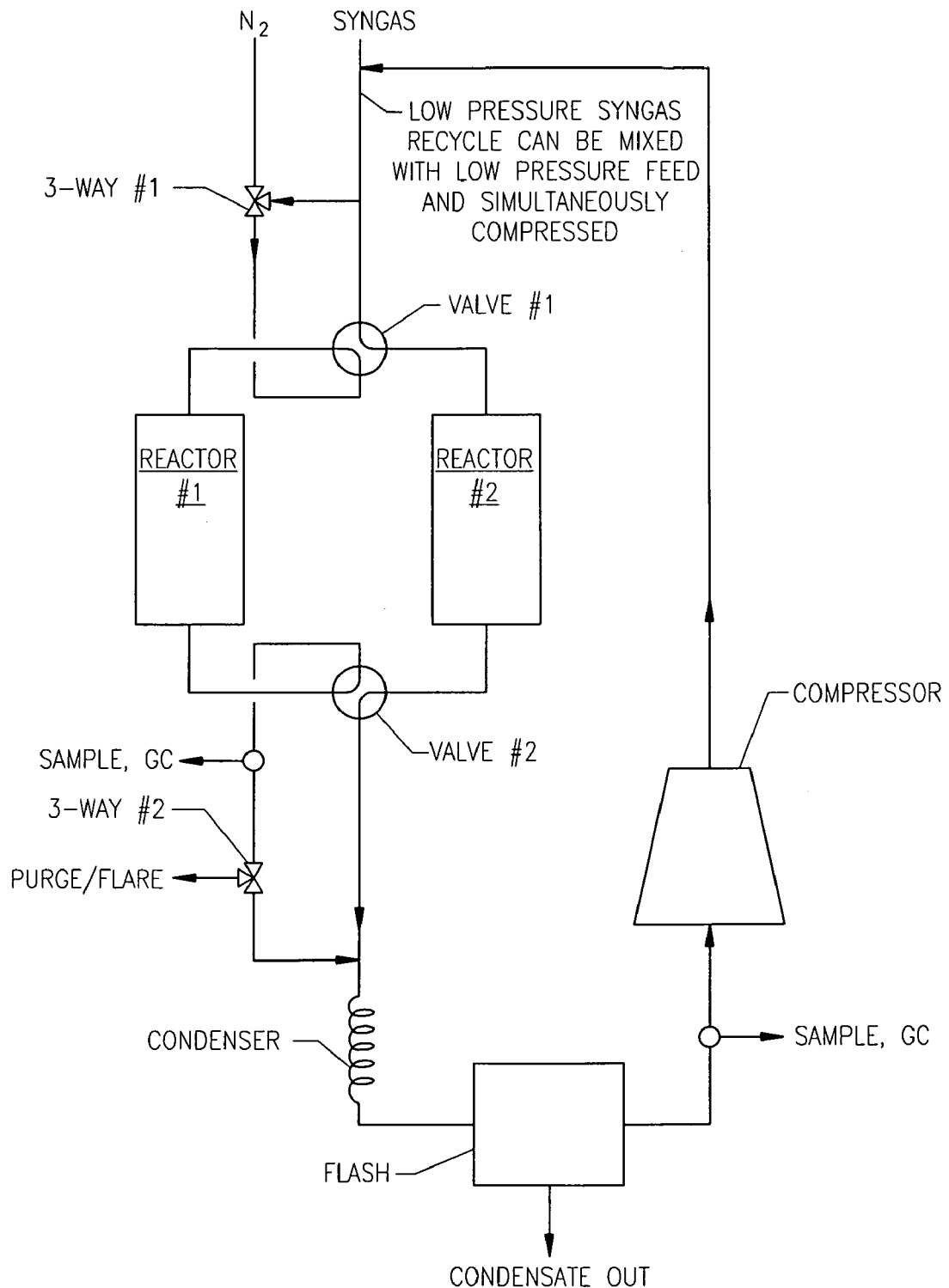
FIG. 2 is a sketch depicting process flows in some embodiments relating to in-situ $CO_2$ removal.

In certain embodiments of the present invention, $CO_2$ is removed in-situ directly after its formation, allowing more formation of alcohols and higher reactor yields. FIG. 2 depicts process flows in some embodiments that utilize in-situ $CO_2$ removal. In some embodiments, owing to the physical and chemical properties of the selected adsorbent material (s), $H_2O$ is also conveniently removed upon its formation. (Water is necessarily produced during the synthesis of higher alcohols from syngas.) Depending on the type of adsorbent used, other unwanted gases such as ethane, ethylene, propane, $SO_2$, and $H_2S$ can be removed (for example, with Zeolite 4A).

In some embodiments described by FIG. 2, multiple reactors or, alternatively, multiple reactor tubes are used. One reactor or a majority of reactor tubes are in operation at preferred temperatures and pressures of operation. One reactor or a minority of reactor tubes is lowered in pressure, increased in temperature, or both to purge $CO_2$ and other adsorbed species from the adsorbent material. All reactors or reactor tubes are in operation at the same time—some making products, and others under regeneration conditions for the adsorbent. The reactor or tubes at high pressure can send products and unused reactants to a flash unit to remove condensable vapors. The reactor or tubes at low pressure send gas, high in $CO_2$ but with other molecular species such as syngas or inert gas, to a flare or furnace for complete combustion. It should be noted that the flash can also be a flash of high pressure and lower temperature, or a combination of lowered temperature and pressure. It is preferred, from a process-efficiency standpoint, to run this flash at high pressures and lowered temperatures.

Figure 3:
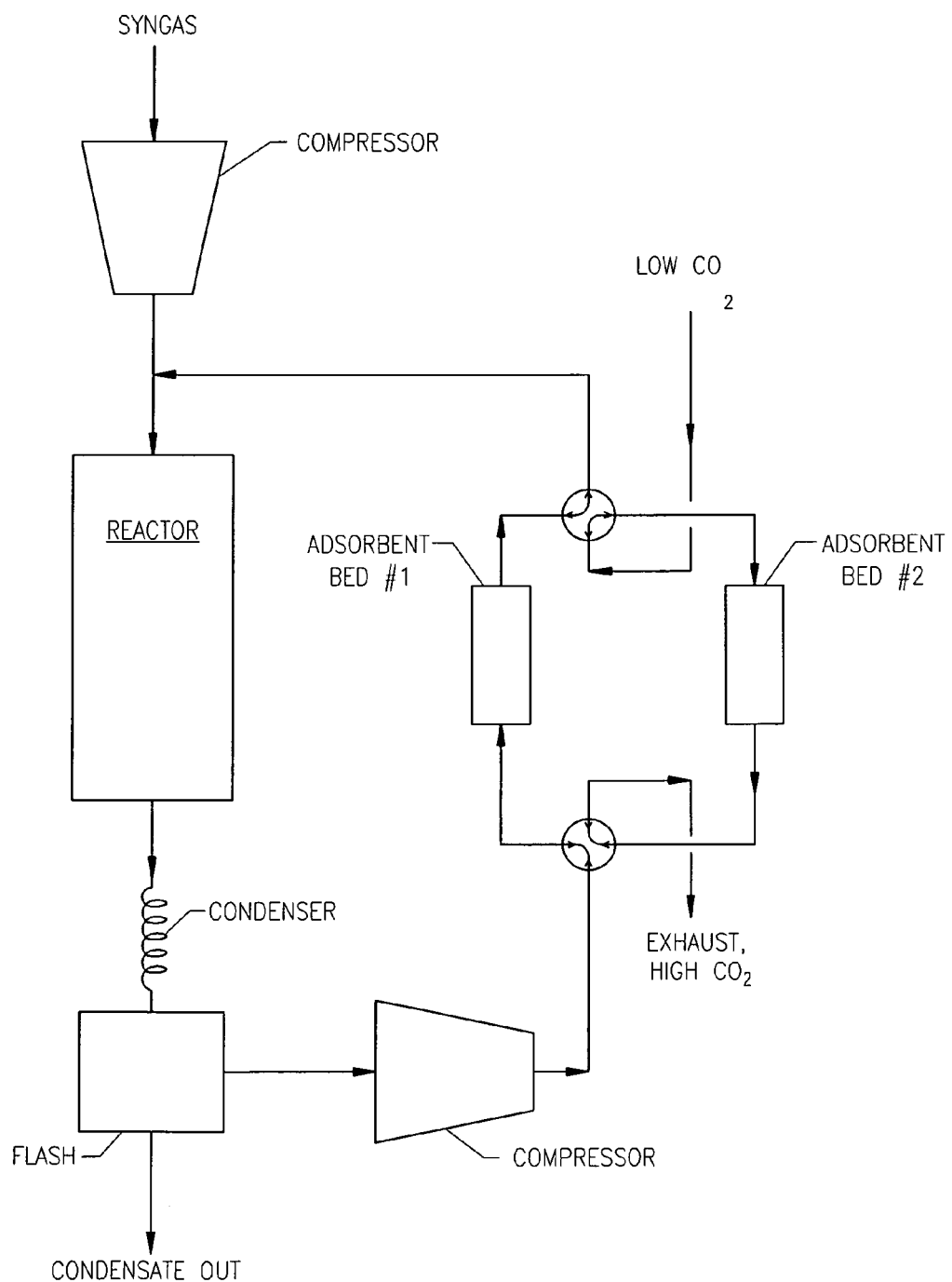
FIG. 3 is a sketch depicting process flows in some embodiments relating to ex-situ $CO_2$ removal.

FIG. 3 shows process flows in some embodiments that utilize ex-situ $CO_2$ removal with pressure-swing adsorption. In these embodiments, a process stream from a reactor is routed to one or more adsorbent beds wherein $CO_2$ can be removed in accordance with the invention as described herein. Ex-situ regeneration is performed preferably after condensable products have been substantially removed from the reactor, such as, for example, in the flash unit depicted in FIG. 3. Depending on the type of adsorbent used, other unwanted gases such as ethane, ethylene, propane, $SO_2$, and $H_2S$ can be removed (for example, with Zeolite 4A).

In some embodiments described by FIG. 3, $CO_2$ is removed ex-situ. The reactor operates and removes condensable vapors, as in other embodiments. After recompression of the recycle stream, the pressurized reactant gas passes through an adsorbent bed, which removes $CO_2$ and possibly hydrocarbons, and mixes with fresh reactor feed before going back to the reactor as a $CO_2$-lean stream. A second adsorbent bed is simultaneously regenerated at low pressure, high temperature, or both. The adsorbent beds can be isolated with valves, so that the recycle loop is always under pressure, and the adsorbent bed under regeneration can be continuously purged with low-pressure inert gas, the effluent being sent to a flare or furnace. As will be recognized, the flash indicated in FIG. 3 need not operate at such a low pressure. It could alternately be operated at lowered temperature, or with a combination of lowered temperature and pressure. It is preferred, from a process-efficiency standpoint, to run this flash at high pressures and low temperatures.

Potential adsorbent materials can be tested for $CO_2$, CO, and $H_2$ adsorption using a thermal gravimetric analyzer (TGA) operated at several temperatures (including reactor temperatures) and partial pressures of gases. These tests yield adsorption isotherms. Mixtures of $CO_2$ and CO can be introduced into a TGA to test the sorption selectivity of the material. Selectivity can be quantified, for example, by saturating the adsorbents with the $CO_2$ and CO mixture(s), purging the TGA with an inert gas, and heating the adsorbent to release the gases which can be quantified by mass spectroscopy. A TGA can be used to determine appropriate desorption/regeneration temperatures for the adsorbent materials at ambient pressure, as will be recognized by a skilled artisan.

The adsorbent materials herein are preferably contained within a reactor. The reactor is any apparatus capable of being effective for producing at least one $C_1$-$C_4$ alcohol from the syngas stream fed. The reactor can be a single vessel or a plurality of vessels. The reactor contains at least one catalyst composition that tends to catalyze the conversion of syngas into $C_2$ and higher alcohols, along with at least one composition having properties associated with adsorbent materials.

The reactor can be engineered and operated in a wide variety of ways. The reactor operation can be continuous, semicontinuous, or batch. Operation that is substantially continuous and at steady state is preferable, especially with continuous removal of unwanted reactor products that could be achieved by utilizing a network of reactors.

For example, in some variations, the reactor comprises a large number of tubes filled with one or more catalysts. In principle, reactants can be fed to a bank of reactor tubes strategically, so that only one or two reactor tubes are offline during adsorbent regeneration.

The flow pattern can be substantially plug flow, substantially well-mixed, or a flow pattern between these extremes. The flow direction can be vertical-upflow, vertical-downflow, or horizontal. A vertical configuration can be preferable.

Any suitable catalyst or combination of catalysts may be used in the reactor to catalyze reactions converting syngas to alcohols. Suitable catalysts for use in the reactor may include, but are not limited to, those disclosed in co-pending and commonly assigned U.S. patent application Ser. No. 12/166, 167. Preferred catalysts increase the rate of formation, selectivity, and/or yield of alcohols. Preferred catalysts also minimize the formation of $CO_2$ and $CH_4$ under reaction conditions that produce alcohols from syngas.

Other suitable catalysts to be activated by the present methods may include alkali/ZnO/$Cr_2O_3$, Cu/ZnO, Cu/ZnO/$Al_2O_3$, CuO/CoO, CuO/CoO/$Al_2O_3$, Co/S, Mo/S, Co/Mo/S, Ni/S, Ni/Mo/S, Ni/Co/Mo/S, Rh/Ti/$SiO_2$, Rh/Mn/$SiO_2$, Rh/Ti/Fe/ Ir/SiO2, Rh/Mn/MCM-41, Cu, Zn, Rh, Ti, Fe, Ir, and mixtures thereof. The addition of basic promoters (e.g., K, Li, Na, Rb, Cs, and Fr) increases the activity and selectivity of some of these catalysts for ethanol or other $C_{2+}$ alcohols. Basic promoters include alkaline-earth and rare-earth metals. Nonmetallic bases can also serve as effective promoters in some embodiments.

In some embodiments, fresh syngas is produced according to methods described in Klepper et al., "METHODS AND APPARATUS FOR PRODUCING SYNGAS," U.S. patent application Ser. No. 12/166,167, the assignee of which is the same as the assignee of the present application. U.S. patent application Ser. No. 12/166,167 is hereby incorporated by reference herein in its entirety.

The syngas entering the reactor is preferably compressed. Generally, catalyst productivity increases with increasing partial pressures of reactants. High reactor inlet pressures realized by the presence of large quantities of unreactive gases are less preferable compared to higher partial pressures of the rate-limiting reactant(s). Conditions effective for producing alcohols from syngas include hydrogen and carbon monoxide partial pressures each about 10-200 atm or higher, preferably each about 25-100 atm. In some embodiments, it is beneficial to employ a higher partial pressure of $H_2$ than that of CO.

The input partial pressures define the feed hydrogen-carbon monoxide molar ratio ($H_2$/CO). While reaction rates are a function of species partial pressures, it can be a matter of convenience to specify $H_2$/CO for reasons of control and optimization within a certain process region. In some embodiments, conditions effective for producing alcohols from syngas include $H_2$/CO from about 0.2-4.0, preferably about 1.0-3.0, and more preferably about 1.5-3.0. These ratios are indicative of certain embodiments and are by no means limiting. It is possible to operate at feed $H_2$/CO ratios less than 0.2 as well as greater than 4, including 5, 10, or even higher. It is well-known that high $H_2$/CO ratios can be obtained with extensive steam reforming and/or water-gas shift in operations prior to the syngas-to-alcohol reactor.

In embodiments wherein $H_2$/CO ratios close to 1:1 are desired for alcohol synthesis, partial oxidation of the carbonaceous feedstock can be utilized, at least in part. In the absence of other reactions, partial oxidation tends to produce $H_2$/CO ratios close to unity, depending on the stoichiometry of the feedstock.

When, as in certain embodiments, relatively low $H_2$/CO ratios are desired, the reverse water-gas shift reaction ($H_2$+$CO_2$→$H_2O$+CO) can potentially be utilized (prior to the syngas-to-alcohol reactor) to consume hydrogen and thus lower $H_2$/CO. In some embodiments, $CO_2$ produced during alcohol synthesis and later released from the adsorbent material can be recycled to the reformer to decrease the $H_2$/CO ratio entering the alcohol-synthesis reactor. Other chemistry and separation approaches can be taken to adjust the $H_2$/CO ratios prior to converting syngas to alcohols, as will be appreciated by the skilled artisan.

In some embodiments, conditions effective for producing alcohols from syngas include reactor temperatures from about 200-400° C., preferably about 250-350° C. Certain embodiments employ reactor temperatures of about 280° C., 290° C., 300° C., 310° C., 320° C., 330° C., or 340° C. Depending on the catalyst chosen, changes to reactor temperature can change conversions, selectivities, and catalyst stability. As is recognized in the art, increasing temperatures can sometimes be used to compensate for reduced catalyst activity over long operating times.

Preferably, the syngas entering the reactor is compressed. Conditions effective for producing alcohols from syngas include reactor pressures from about 20-500 atm, preferably about 50-200 atm or higher. Generally, productivity increases with increasing reactor pressure, and pressures outside of these ranges can be employed with varying effectiveness.

In some embodiments, conditions effective for producing alcohols from syngas include average reactor residence times from about 0.1-10 seconds, preferably about 0.5-2 seconds. "Average reactor residence time" is the mean of the residence-time distribution of the reactor contents under actual operating conditions. Catalyst contact times can also be calculated by a skilled artisan and these times will typically also be in the range of 0.1-10 seconds, although it will be appreciated that it is certainly possible to operate at shorter or longer times.

The catalyst phase can be a packed bed or a fluidized bed. The catalyst particles can be sized and configured such that the chemistry is, in some embodiments, mass-transfer limited or kinetically limited. The catalyst can take the form of a powder, pellets, granules, beads, extrudates, and so on. When a catalyst support is optionally employed, the support may assume any physical form such as pellets, spheres, monolithic channels, etc. The supports may be coprecipitated with active metal species or the support may be treated with the catalytic metal species and then used as is or formed into the aforementioned shapes. In some variations, the support may be formed into the aforementioned shapes and then treated with the catalytic species.

Reaction selectivities can be calculated on a carbon-atom basis. "Carbon-atom selectivity" means the ratio of the moles of a specific product to the total moles of all products, scaled by the number of carbon atoms in the species. This definition accounts for the mole-number change due to reaction, and best describes the fate of the carbon from converted CO. The selectivity $S_j$ to general product species $C_{x_j}H_{y_j}O_{z_j}$ is $$S_j = \frac{x_j F_j}{\sum_i x_i F_i}$$

wherein $F_j$ is the molar flow rate of species j which contains $x_j$ carbon atoms. The summation is over all carbon-containing species ($C_{x_i}H_{y_i}O_{z_i}$) produced in the reaction. In some embodiments, wherein all products are identified and measured, the individual selectivities sum to unity (plus or minus analytical error). In other embodiments, wherein one or more products are not identified in the exit stream, the selectivities can be calculated based on what products are identified, or are instead based on the conversion of CO.

In various embodiments of the present invention, the product stream from the reactor may be characterized by reaction selectivities of about 10-60% or higher to methanol and about 10-50% or higher to ethanol. The product stream from the reactor may include up to, for example, about 25% reaction selectivity to $C_{3+}$ alcohols, and up to about 10% to other non-alcohol oxygenates such as aldehydes, esters, carboxylic acids, and ketones. These other oxygenates can include, for example, acetone, 2-butanone, methyl acetate, ethyl acetate, methyl formate, ethyl formate, acetic acid, propanoic acid, and butyric acid.

In general, the specific selection of catalyst configuration (geometry), $H_2$/CO ratio, temperature, pressure, and residence time (or feed rate) will be selected to provide, or will be subject to constraints relating to, an economically optimized process. The plurality of reactor variables and other system parameters can be optimized, in whole or in part, by a variety of means.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

Therefore, to the extent there are variations of the invention which are within the spirit of the disclosure or equivalent to the inventions found in the appended claims, it is the intent that this patent will cover those variations as well. The present invention shall only be limited by what is claimed.

What is claimed is:

1. A method for producing one or more $C_1$-$C_4$ alcohols from syngas, said method comprising:
   (i) converting a portion of said syngas into one or more $C_1$-$C_4$ alcohols using a first composition that can catalyze the conversion of syngas to $C_1$-$C_4$ alcohols under reaction conditions in a reactor;
   (ii) capturing a portion of the carbon dioxide produced or present using a second composition that is capable of adsorbing carbon dioxide in-situ under said reaction conditions, wherein said second composition is substantially chemically inert under said reaction conditions; and
   (iii) releasing at least some of said carbon dioxide from said second composition under regeneration conditions,
   wherein said first composition and said second composition are both contained in said reactor, each of said first and second compositions being present in solid form, and
   wherein said reaction conditions are different from said regeneration conditions.

2. The method of claim 1, wherein said second composition comprises a zeolite.

3. The method of claim 2, wherein said zeolite is selected from the Faujasite structure class.

4. The method of claim 2, wherein said zeolite is Zeolite 4A.

5. The method of claim 3, wherein said zeolite is Zeolite 13X.

6. The method of claim 1, wherein said second composition does not include a zeolite.

7. The method of claim 6, wherein said second composition comprises calcium oxide.

8. The method of claim 1, wherein said second composition is capable of being regenerated by decreasing pressure and/or increasing temperature.

9. The method of claim 1, wherein said first and second compositions are combined prior to loading into said reactor.

10. The method of claim 1, wherein at least some of said first and second compositions are layered inside said reactor.

11. The method of claim 1, wherein said second composition resides substantially adjacent to an outlet of said reactor.

12. The method of claim 1, wherein said second composition is present in the form of pellets.

13. The method of claim 1, wherein said step (iii) is conducted in-situ inside said reactor.

14. The method of claim 1, wherein said step (iii) is conducted ex-situ from said reactor.

15. The method of claim 1, wherein said step (iii) further comprises placing said reactor under a substantially inert gas.

16. The method of claim 1, wherein said step (iii) comprises a reduction in pressure.

17. The method of claim 1, wherein said step (iii) comprises an increase in temperature.

18. A method of producing one or more $C_1$-$C_4$ alcohols from syngas, said method comprising repeating steps (i)-(iii) of claim 1.

19. The method of claim 1, wherein during step (ii), at least some water produced or present is adsorbed onto said second composition.

20. The method of claim 1, wherein during step (ii), said second composition adsorbs one or more species selected from the group consisting of methane, ethane, ethylene, propane, sulfur dioxide, and hydrogen sulfide.

21. The method of claim 14, wherein said step (iii) comprises pressure-swing adsorption.

22. The method of claim 14, further comprising removal of at least one condensable species from said reactor prior to conducting step (iii).

23. The method of claim 1, wherein step (ii) captures at least 80% of the carbon dioxide present in the stream from step (i).

24. The method of claim 23, wherein step (iii) releases at least 90% of the carbon dioxide captured in step (ii).

25. The method of claim 24, wherein step (ii) captures at least 90% of the carbon dioxide present in the stream from step (i), and wherein step (iii) releases at least 95% of the carbon dioxide captured in step (ii).

26. A method for producing ethanol from syngas, said method comprising:
   (i) converting a portion of said syngas into ethanol using a catalyst composition that can catalyze the conversion of syngas to ethanol under reaction conditions in a reactor;
   (ii) capturing a portion of the carbon dioxide produced or present using an adsorbent composition contained in said reactor, wherein said adsorbent composition is capable of adsorbing carbon dioxide in-situ under said reaction conditions and is substantially chemically inert under said reactor conditions; and
   (iii) releasing at least some of said carbon dioxide from said second composition under regeneration conditions comprising a lower pressure and/or a higher temperature than said reaction conditions,
   wherein each of said catalyst composition and adsorbent composition is present in solid form.

* * * * *